(12) United States Patent
Park et al.

(10) Patent No.: US 11,927,764 B2
(45) Date of Patent: Mar. 12, 2024

(54) HEAD MOUNTED DISPLAY DEVICE

(71) Applicant: MEGAGEN IMPLANT CO., LTD., Daegu (KR)

(72) Inventors: Kwang Bum Park, Daegu (KR); Hyun Wook An, Daegu (KR); Keun Oh Park, Daegu (KR); Tae Gyoun Lee, Daegu (KR)

(73) Assignee: MEGAGEN IMPLANT CO., LTD. (KR)

( * ) Notice: Subject to any disclaimer, the term of this patent is extended or adjusted under 35 U.S.C. 154(b) by 0 days.

(21) Appl. No.: 18/025,395

(22) PCT Filed: Aug. 24, 2021

(86) PCT No.: PCT/KR2021/011297
§ 371 (c)(1),
(2) Date: Mar. 8, 2023

(87) PCT Pub. No.: WO2022/055153
PCT Pub. Date: Mar. 17, 2022

(65) Prior Publication Data
US 2023/0324700 A1 Oct. 12, 2023

(30) Foreign Application Priority Data
Sep. 14, 2020 (KR) .................. 10-2020-0117944

(51) Int. Cl.
*G02B 27/01* (2006.01)
*A61B 34/10* (2016.01)

(52) U.S. Cl.
CPC .......... *G02B 27/0176* (2013.01); *A61B 34/10* (2016.02); *A61B 2034/102* (2016.02); *A61B 2034/107* (2016.02); *G02B 2027/0154* (2013.01)

(58) Field of Classification Search
CPC ........ G02B 27/0176; G02B 2027/0154; A61B 34/10; A61B 2034/102; A61B 2034/107
See application file for complete search history.

(56) References Cited

U.S. PATENT DOCUMENTS 10,353,206 B2   7/2019   Guo et al.
10,617,025 B1 * 4/2020   Chen .................... H05K 5/0217
(Continued)

FOREIGN PATENT DOCUMENTS

JP        4023412 B2    12/2007
JP     2009033308 A     2/2009
(Continued)

OTHER PUBLICATIONS

International Search Report for PCT/KR2021/011297, dated Nov. 30, 2021.

*Primary Examiner* — David Tung
(74) *Attorney, Agent, or Firm* — Renaissance IP Law Group LLP

(57) ABSTRACT

Disclosed is a head mounted display device. The head mounted display device includes a head mount unit wearable on a head of a user, a display unit supported on the head mount unit and sending an image to eyes of the user, and a position adjustment unit coupled to the head mount unit, connected to the display unit, and moving the display unit relative to the head mount unit such that a position of the display unit varies with respect to the eyes of the user.

7 Claims, 9 Drawing Sheets

(56) References Cited

U.S. PATENT DOCUMENTS

| | | | |
|---|---|---|---|
| 2006/0119539 A1* | 6/2006 | Kato | G02B 27/0176 345/8 |
| 2011/0273365 A1* | 11/2011 | West | G02B 27/0176 29/428 |
| 2012/0002046 A1* | 1/2012 | Rapoport | G02B 27/0176 348/E7.091 |
| 2012/0050144 A1* | 3/2012 | Morlock | G06T 19/006 345/8 |
| 2014/0176398 A1 | 6/2014 | West et al. | |
| 2017/0017085 A1* | 1/2017 | Araki | G02B 27/028 |
| 2017/0052378 A1* | 2/2017 | Yang | H04R 1/105 |
| 2019/0179409 A1* | 6/2019 | Jones | G02B 27/0172 |
| 2019/0331928 A1* | 10/2019 | Lin | G02C 11/08 |
| 2020/0400934 A1* | 12/2020 | Appel | G02B 23/125 |

FOREIGN PATENT DOCUMENTS

| | | |
|---|---|---|
| JP | 5476036 B2 | 4/2014 |
| KR | 20170086557 A | 7/2017 |
| KR | 20190141911 A | 12/2019 |

\* cited by examiner

HEAD MOUNTED DISPLAY DEVICE

TECHNICAL FIELD

The present inventive concept relates to a head mounted display device, and more particularly, to a head mounted display device which can assist an accurate treatment by a user in a dental implant treatment process.

BACKGROUND ART

Generally, augmented reality (AR) means providing a virtual image or an image generated by a computer and the like by being overlapped with an actual image of a real world.

In order to realize such AR, an optical system capable of overlapping a virtual images or image generated by a device such as a computer with an image of the real world is necessary. As the optical system, a technology using an optical means such as a prism that reflects or refracts a virtual image by using a head mounted display (HMD) device or a glasses-type device has been known.

On the other hand, while a dental implant originally means a substitute for restoring lost human tissue, in dentistry, it refers to a series of treatments for implanting artificial teeth. It is a treatment to restore the function of a tooth by placing a fixture that is a tooth root made of titanium and the like, exhibiting no rejection to the human body, to replace a lost tooth root (root), in the alveolar bone where the tooth is missing, and fixing the artificial tooth.

While a general prosthesis or denture damages surrounding teeth or bones over time, the implant does not damage surrounding teeth tissue, and may be used semi-permanently because no tooth decay occurs while maintaining the same functions or shapes as natural teeth.

A prosthetic tooth treatment (also known as an implant or dental implant treatment) varies depending on the type of fixture, but it is generally completed by drilling a placement position using a predetermined drill, placing a fixture in the alveolar bone to be osseointegrated therein, combining an abutment to the fixture, and capping the abutment with the final prosthesis.

Dental implants are used to restore single missing teeth, as well as to improve the function of dentures for partially and completely edentulous patients, to improve the aesthetics of prosthetic restorations, and to help stabilize the dentition while distributing excessive stress applied to the surrounding supporting bone tissue.

The dental implant generally includes a fixture implanted as an artificial tooth root, an abutment coupled to the fixture, an abutment screw for securing the abutment to the fixture, and an artificial tooth coupled to the abutment. Here, the abutment may be coupled to the fixture and a coupled state may be maintained before the abutment is coupled to the fixture, that is, during the period of time until the osseointegration of the fixture in the alveolar bone.

The fixture, which is a component of a dental implant, is a part of the implant that is placed in a drill hole in the alveolar bone at a location where the implant is to be placed, and serves as the artificial tooth root. Therefore, the fixture is firmly embedded in the alveolar bone. Accordingly, a threaded portion (thread) is formed on the outer surface of the fixture so that the fixture can be firmly attached to the inner wall portion of the alveolar bone forming the drill hole. This threaded portion is not only inserted in the alveolar bone to ensure that the fixture and the alveolar bone are firmly bonded to each other, but also serves to increase a contact area between the fixture and the alveolar bone, thereby strengthening the fixation force of the fixture to the alveolar bone, especially the initial stability.

As such, the dental implant treatment is performed by drilling a hole in the alveolar bone using a drill, placing a fixture in the drilled hole, coupling the abutment with the fixture after the osseointegration, and finally capping an artificial tooth (prosthesis).

In such a conventional dental implant treatment, the drilling of the alveolar bone often relies on the surgeon's sense of hand. This treatment by hand sense relies on the operator's motor skills and spatial perception skills, and thus, it is difficult to achieve a high degree of accuracy.

In particular, due to human physiological limitations, it is very difficult to achieve the ideal three-dimensional angle of a handpiece drill, so many dentists, except for a few "craftsmen" with special talents and many years of experience, have difficulty reproducing the ideal three-dimensional angle.

Therefore, there is a demand for the development of video guidance technology that can perform the treatment while checking whether a drilling direction and angle and the like are accurately proceeding with a pre-planned direction and angle and the like in real-time video information until the drilling work on the alveolar bone is completed.

In particular, when the treatment is guided through the HMD device using the AR described above, the user's (operator's) line of sight does not deviate from the treatment site, thus making the treatment process convenient and greatly increasing the accuracy of the treatment.

However, each user using the HMD device will have a different body size (the head size, the position of eyes on the face, etc.), and as a result, there are many problems in that the image may be out of focus depending on the user.

DETAILED DESCRIPTION OF THE INVENTIVE CONCEPT

Technical Problem

Provided is a head mounted display device capable of adjusting the position and angle of a display device to cope with the different eye positions of users.

According to one aspect of the disclosure, head mounted display device includes a head mount unit wearable on a head of a user, a display unit supported on the head mount unit and sending an image to eyes of the user, and a position adjustment unit coupled to the head mount unit, connected to the display unit, and moving the display unit relative to the head mount unit such that a position of the display unit varies with respect to the eyes of the user.

The position adjustment unit may include a movement module moving the display unit in a direction approaching or receding from the head mount unit, and a rotation module connected to the movement module and rotating the display unit with respect to the head mount unit.

The movement module may include a first connection arm connected to the head mount unit, a second connection arm connected to the display unit, and a moving block coupled to the second connection arm and coupled to the first connection arm to be movable relative thereto.

A first insertion hole, in which one end portion of the moving block is inserted, may be formed in the first connection arm, and a second insertion hole, in which the other end portion of the moving block is inserted, may be formed in the second connection arm.

A plurality of locking recesses may be formed in any one of one surface of the moving block and an inner wall surface of the first insertion hole, and a plurality of locking protrusions inserted in the locking recesses may be formed on the other of the one surface of the moving block and the inner wall surface of the first insertion hole.

The locking recesses may be formed in one surface of the moving block, and the locking protrusions may be formed on the inner wall surface of the first insertion hole.

The rotation module may be coupled to the second connection arm and may include a hinge axis portion to which the display unit is rotatably coupled.

The head mount unit may include a mount main body portion to which the position adjustment unit is connected, and which may be formed in a ring shape so that the head of the user passes therethrough, a movable pad portion connected to the mount main body portion and moving in a direction approaching or receding from an inner wall surface of the mount main body portion, and a pad adjustment portion supported on the mount main body portion, connected to the movable pad portion, and moving the movable pad portion.

The display unit may include a display frame portion connected to the position adjustment unit, a source portion mounted on the display frame portion and outputting the image, and an optical portion supported on the display frame portion and transferring the image output from the source portion to the eyes of the user by reflecting the image.

The head mounted display device may further include a face shield detachably attached to the display unit and shielding the face of the user.

The head mounted display device may further include a marker coupled to the head mount unit and recognized by an external detector.

Advantageous Effects

According to the present inventive concept, as the position adjustment unit moves the display unit relative to the head mount unit so that the position of the display unit can vary with respect to the eyes of a user, the position of the display unit with respect to the eyes of a user may be adjusted, and thus, the position and angle of the display unit are adjusted corresponding to the different eye positions for different users, thereby increasing image recognition by a user.

MODE OF THE INVENTIVE CONCEPT

In order to fully understand the operational advantages of the present inventive concept and the objectives achieved by the implementation of the present inventive concept, the accompanying drawings illustrating preferred embodiments of the present inventive concept and the contents described in the accompanying drawings are referred to.

Hereinafter, the inventive concept will be described in detail by explaining preferred embodiments of the inventive concept with reference to the attached drawings. In the following description, when detailed descriptions about related well-known functions or structures are determined to make the gist of the disclosure unclear, the detailed descriptions will be omitted herein.

Figure 1:
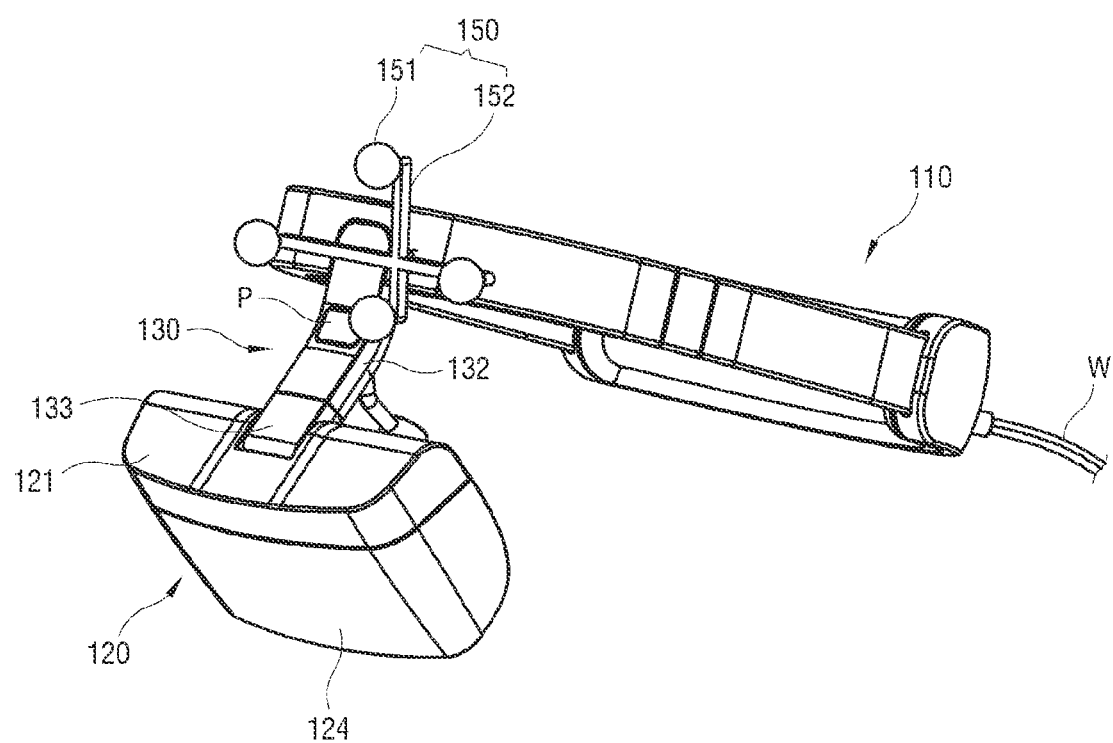
FIG. 1 is a view illustrating a head mounted display device according to an embodiment of the disclosure.
Figure 2:
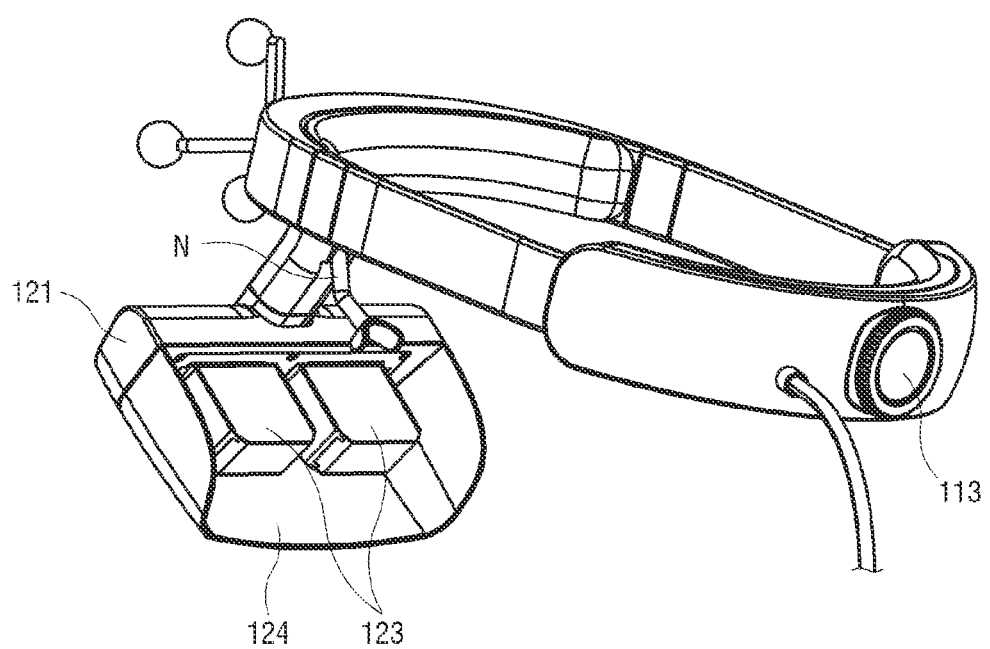
FIG. 2 is a view when the head mounted display device of FIG. 1 is viewed from a different direction.
Figure 3:
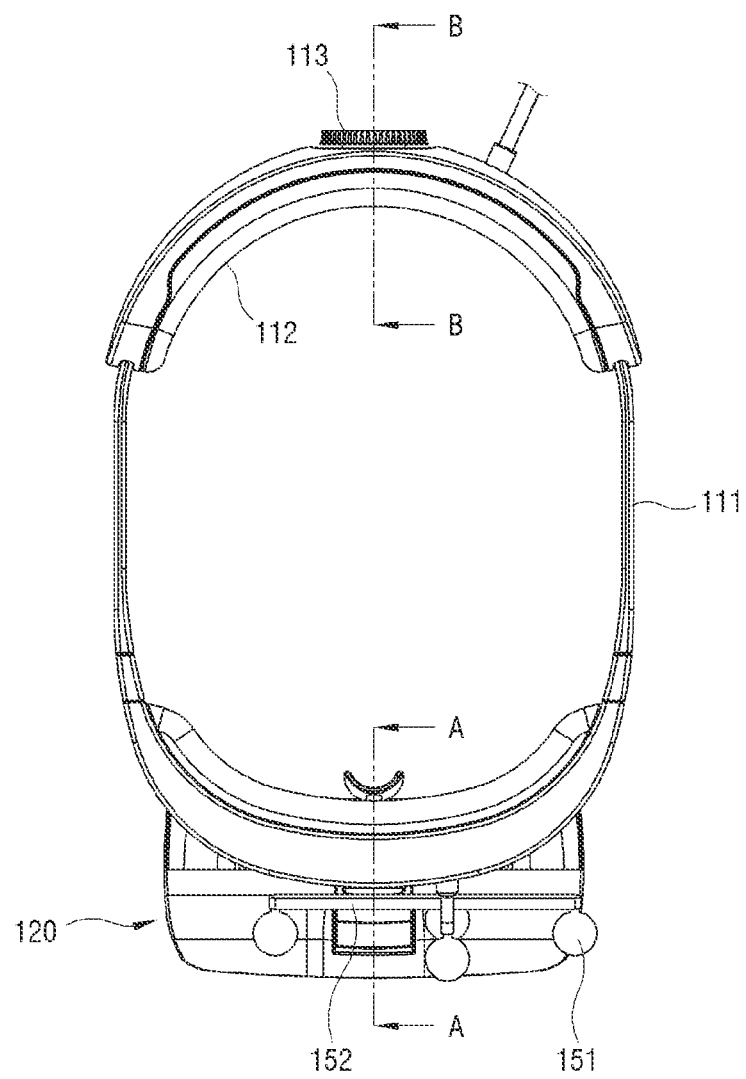
FIG. 3 is a plan view of FIG. 1.
Figure 4:
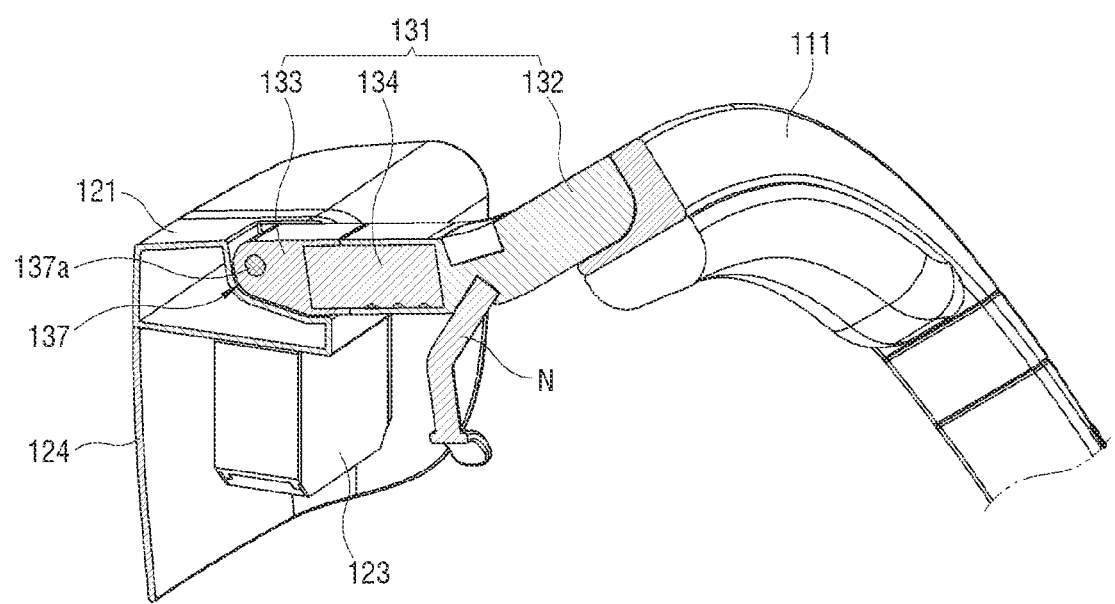
FIG. 4 is a cross-sectional view taken along line A-A of FIG. 3.
Figure 5:
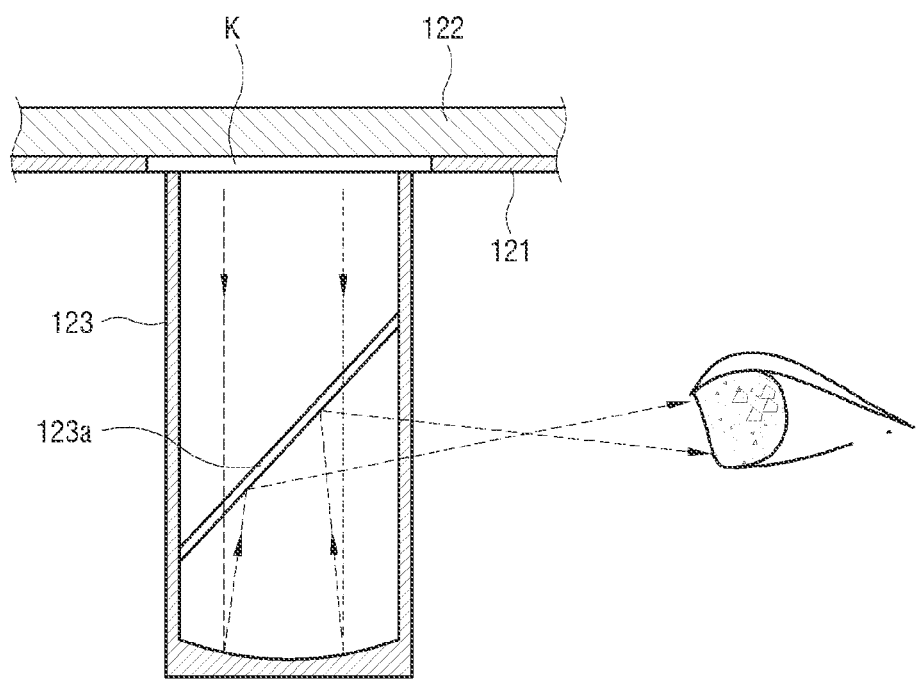
FIG. 5 is a view illustrating the interior of a display unit of FIG. 1.
Figure 6:
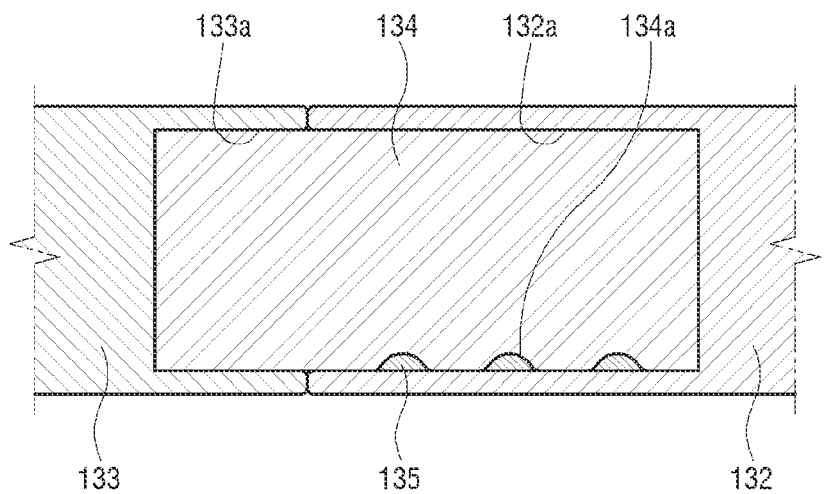
FIG. 6 is a view illustrating the interior of a position adjustment unit of FIG. 1.
Figure 7:
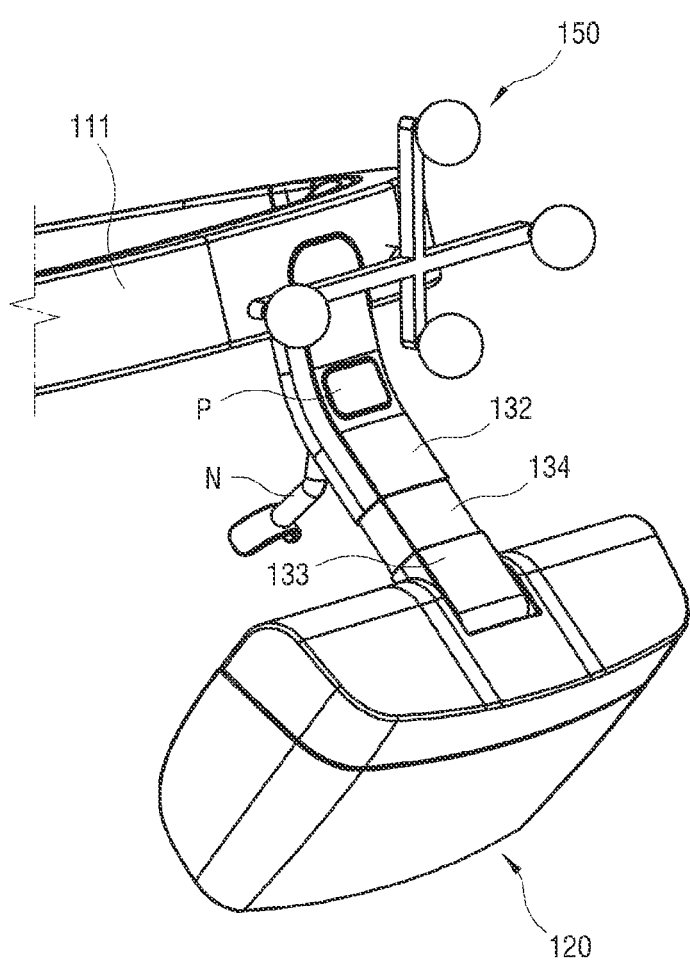
FIG. 7 is a view illustrating a state in which the position of the display unit in FIG. 1 is moved.
Figure 8:
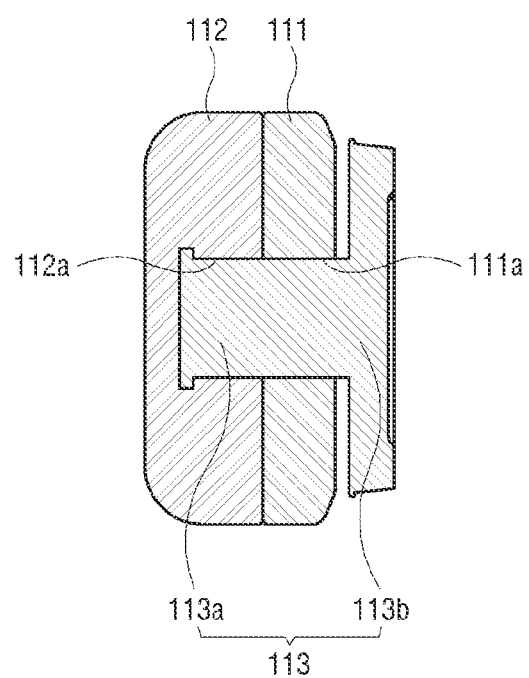
FIG. 8 is a cross-sectional view taken along line B-B of FIG. 3.
Figure 9:
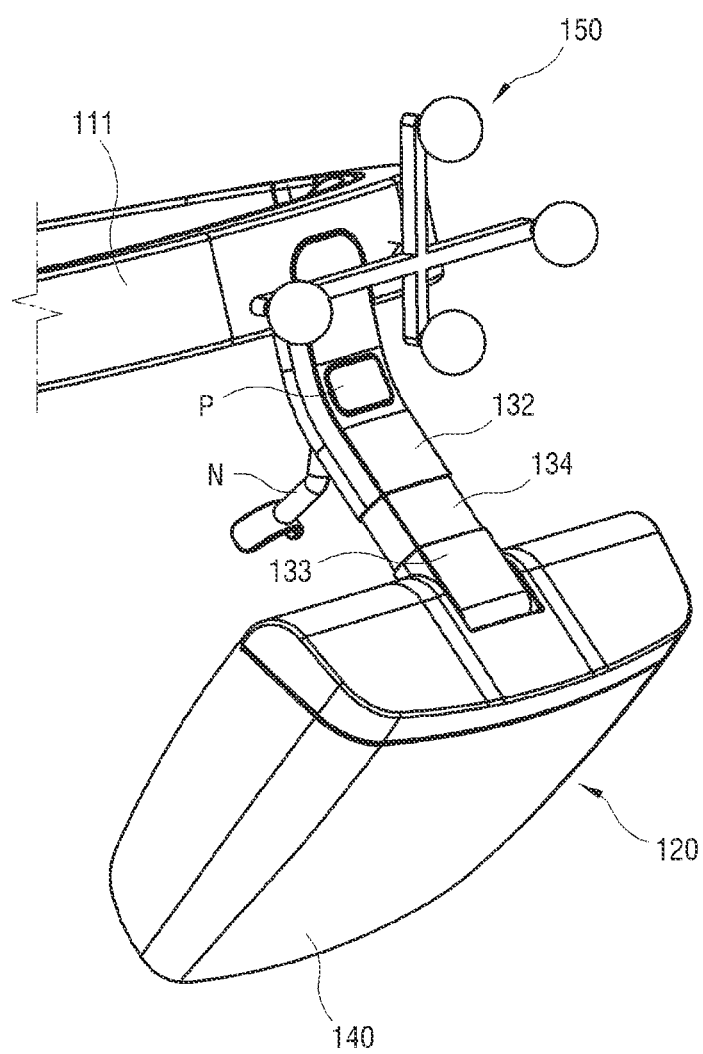
FIG. 9 is a view illustrating a state in which a face shield is attached to the display unit of FIG. 7.

FIG. 1 is a view illustrating a head mounted display device according to an embodiment of the disclosure, FIG. 2 is a view when the head mounted display device of FIG. 1 is viewed from a different direction, FIG. 3 is a plan view of FIG. 1, FIG. 4 is a cross-sectional view taken along line A-A of FIG. 3, FIG. 5 is a view illustrating the interior of a display unit of FIG. 1, FIG. 6 is a view illustrating the interior of a position adjustment unit of FIG. 1, FIG. 7 is a view illustrating a state in which the position of the display unit in FIG. 1 is moved, FIG. 8 is a cross-sectional view taken along line B-B of FIG. 3, and FIG. 9 is a view illustrating a state in which a face shield is attached to the display unit of FIG. 7.

In the head mounted display device according to the present embodiment, the position and angle of an image transmitted corresponding to the different eye positions for different users are adjusted, thereby increasing image recognition by a user.

To this end, the head mounted display device according to the present embodiment includes, as illustrated in FIGS. 1 to 9, a head mount unit 110, a display unit 120, a position adjustment unit 130, a face shield 140, a marker 150, and a nose rest N.

The head mount unit 110 may be worn on the head of a user. The head mount unit 110 includes a mount main body portion 111, to which the position adjustment unit 130 is connected, and formed in a ring shape so that the user's head can pass therethrough, a movable pad portion 112 connected to the mount main body portion 111 and moving in a direction approaching or receding from an inner wall surface of the mount main body portion 111, and a pad adjustment portion 113 supported on the mount main body portion 111 and connected to the movable pad portion 112 to move the movable pad portion 112.

The mount main body portion 111 is formed in a shape similar to a circular ring, as illustrated in FIGS. 1 to 3. The user's head is located inside the mount main body portion 111.

The movable pad portion 112 is connected to the mount main body portion 111. The movable pad portion 112 is connected to the occiput of a user. To safely support the user's occiput on the movable pad portion 112, the movable pad portion 112 is formed in a curved shape corresponding to the occipital shape.

The movable pad portion 112 according to the present embodiment may move in the direction approaching or receding from the inner wall surface of the mount main body portion 111. When the size of a user's head is slightly smaller than the mount main body portion 111, the movable pad portion 112 moves in a direction receding from the inner wall surface of the mount main body portion 111, and when the user's head size is slightly larger than the mount main body portion 111, the movable pad portion 112 moves in a direction approaching the inner wall surface of the mount main body portion 111.

In the movable pad portion 112 according to the present embodiment, a guide bar (not shown) protrudes from a rear surface of the movable pad portion 112 and is inserted in a guide hole (not shown) formed in the mount main body portion 111.

An insertion hole 112a, in which an adjustment body portion 113a of the pad adjustment portion 113 to be described below is inserted, is formed in the movable pad portion 112. A thread is not formed on an inner circumferential surface of the insertion hole 112a.

The pad adjustment portion 113 is supported on the mount main body portion 111. The pad adjustment portion 113 is connected to the movable pad portion 112 to move the movable pad portion 112.

The pad adjustment portion 113 according to the present embodiment includes the adjustment body portion 113a meshed with a screw hole 111a formed in the mount main body portion 111 and coupled to the movable pad portion 112 to be rotatable relative thereto, and an adjustment handle portion 113b coupled to the adjustment body portion 113a.

The adjustment handle portion 113b is formed in a circular disc shape. The adjustment handle portion 113b is coupled to the adjustment body portion 113a, and thus, the adjustment body portion 113a is rotated by the rotation of the adjustment handle portion 113b.

The adjustment body portion 113a is formed in a circular rod shape. A thread to be meshed with the thread formed on an inner circumferential surface of the screw hole 111a is formed on an outer circumferential surface of the adjustment body portion 113a. Accordingly, the adjustment body portion 113a may move back and forth by the rotation of the adjustment body portion 113a.

As the front end portion of the adjustment body portion 113a is inserted in the insertion hole 112a and coupled to the movable pad portion 112 to be rotatable relative thereto, while not being rotated by the rotation of the adjustment body portion 113a, the movable pad portion 112 may be moved by the movement of the adjustment body portion 113a in the direction approaching or receding from the inner wall surface of the mount main body portion 111. In the movement process described above, as the guide bar is inserted in the guide hole, the movable pad portion 112 may move back and forth while not being rotated by the rotation of the adjustment body portion 113a.

Meanwhile, the display unit 120 is supported on the head mount unit 110. The display unit 120 sends an image to the eyes of a user. The display unit 120 according to the present embodiment includes, as illustrated in FIGS. 1 to 5, a display frame portion 121 connected to the position adjustment unit 130, a source portion 122 mounted on the display frame portion 121 and outputting an image, an optical portion 123 supported on the display frame portion 121 and transferring the image to the eyes of a user by reflecting the image output from the source portion 122, and a goggle portion 124 coupled to the display frame portion 121.

The display frame portion 121 is connected to the position adjustment unit 130. The source portion 122 is arranged inside the display frame portion 121. A cut hole K formed in the display frame portion 121 according to the present embodiment so that the source portion 122 and the optical portion 123 are connected to each other.

The display frame portion 121 may be made of an iron material that is responsive to a magnetic force, or may include an attachment induction portion (not shown) for an iron material, for the attachment of the face shield 140.

The source portion 122 outputs an image by receiving information such as a guide image (for example, an image showing an ideal angle of a handpiece drill (not shown) and the like) generated by a separate treatment guide device (not shown) in a wireless or wired manner. In the present embodiment, the source portion 122 is arranged in an upper area of the optical portion 123. The source portion 122 includes a circuit board (not shown) on which a plurality of electronic devices (not shown) are mounted.

The optical portion 123 is coupled to the display frame portion 121. The optical portion 123 reflects the image output from the source portion 122 and transfers the image to the eyes of a user. In the present embodiment, at least a portion of the optical portion 123 is made of a transparent material so that a user may visually recognize objects in front of the user. The optical portion 123 includes a mirror portion 123a that reflects the image output from the source portion 122 and transfers the image to the eyes of the user. The mirror portion 123a is provided to be transparent to pass light and also reflect light (as light is reflected by a glass window). Through the mirror portion 123a, the user may visually recognize actual objects located in front of the user and simultaneously visually recognize the image reflected by the mirror portion 123a and transferred to the eyes of the user to be overlapped with the actual objects.

Furthermore, as illustrated in FIG. 5, a lower inner wall surface of the optical portion 123 may reflect the image output from the source portion 122 to the mirror portion 123a.

The goggle portion 124 is coupled to the display frame portion 121. The goggle portion 124 is made of a transparent material. In the present embodiment, the goggle portion 124 protects the optical portion 123 from the outside, thereby preventing foreign materials such as water from adhering to the optical portion 123 in a treatment process.

Meanwhile, the position adjustment unit 130 is coupled to the head mount unit 110 and connected to the display unit 120. The position adjustment unit 130 may move the display unit 120 relative to the head mount unit 110 so that the position of the display unit 120 may vary with respect to the eyes of a user.

The position adjustment unit 130 according to the present embodiment includes, as illustrated in FIGS. 1 to 4, a movement module 131 moving the display unit 120 in a direction approaching or receding from the head mount unit 110, and a rotation module 137 connected to the movement module 131 and rotating the display unit 120 with respect to the head mount unit 110.

The movement module 131 moves the display unit 120 in a direction approaching or receding from the head mount unit 110.

The movement module 131 includes, as illustrated in FIGS. 1 to 9, a first connection arm 132 connected to the head mount unit 110, a second connection arm 133 coupled to the display unit 120, and a moving block 134 coupled to the second connection arm 133 and coupled to the first connection arm 132 to be movable relative thereto.

The first connection arm 132 is coupled to the mount main body portion 111 of the head mount unit 110. A first insertion hole 132a, in which one end portion of the moving block 134 is inserted, is formed in the first connection arm 132. A locking protrusion 135 protrudes from an inner wall surface of the first insertion hole 132a. In the present embodiment, the locking protrusion 135 includes a plurality of locking protrusions which are spaced apart from each other.

The second connection arm 133 is connected to the display frame portion 121 of the display unit 120. A second insertion hole 133a in which the other end portion of the moving block 134 is inserted and fixed is formed in the second connection arm 133.

The moving block 134 is inserted in the second insertion hole 133a to be fixed to the second connection arm 133, and inserted in the first insertion hole 132a to be movable relative to the first connection arm 132. A plurality of locking recesses 134a inserted in the locking protrusions 135 are formed in a lower surface of the moving block 134.

In the present embodiment, when the display unit 120 needs to be away from the eyes of a user for the position adjustment of the display unit 120, the user holds and pushes the display unit 120 in a direction away from the eyes of a user. Through the operation, the moving block 134 is moved in a direction away from the first insertion hole 132a.

In contrast, when the display unit 120 needs to be close to the eyes of a user, the user holes and pushes the display unit 120 in a direction approaching the eyes of a user. Through the operation, the moving block 134 is moved in a direction to be inserted into the first insertion hole 132a.

In the movement process of the moving block 134, as the locking protrusions 135 are inserted in the neighboring locking recesses 134a, the movement of the moving block 134 is made step by step.

The moving block 134 may be formed of an elastic material to prevent the locking recesses 134a and the locking protrusion 135 from being damaged in the repeated movement process of the moving block 134 for the position adjustment.

Also, the movement module 131 may further include a hook portion (not shown) hook-coupled to the moving block 134 and an adjustment button P connected to the hook portion to have the hook portion coupled to or decoupled from the moving block 134.

The rotation module 137 is connected to the movement module 131. The rotation module 137 rotates the display unit 120 with respect to the head mount unit 110. In the present embodiment, the rotation module 137 is coupled to the second connection arm 133 and includes a hinge axis portion 137a to which the display frame portion 121 of the display unit 120 is rotatably coupled.

In the present embodiment, an insertion hole (not shown), in which the hinge axis portion 137a is inserted, is formed in the display frame portion 121. The rotation of the display unit 120 is restricted by a frictional force between an inner wall surface of the insertion hole and an outer circumferential surface of the hinge axis portion 137a, and the display unit 120 is rotated only when the user rotates the display unit 120 by applying a force thereto.

Meanwhile, the face shield 140 is detachably attached to the display unit 120 to overlap the goggle portion 124. The face shield 140 shields the face of a user. In the present embodiment, a magnet (not shown) is provided in an upper area of the face shield 140 and may be attached to the display frame portion 121 by a magnetic force.

As such, as the head mounted display device according to the present embodiment includes the face shield 140 that shields the face of a user and is detachably coupled to the display unit 120, the face of a user may be shielded as necessary, and thus, the saliva of one receiving a treatment or water may be prevented from adhering to the face of a user. Accordingly, a user may be prevented from being infected with infectious diseases and the like in the treatment process.

Meanwhile, the marker 150 is coupled to the head mount unit 110. The marker 150 may be recognized by an external detector (not shown). The external detector may include a camera that visually recognize the marker 150. The external detector obtains position information of the head mounted display device by recognizing the marker 150, and the position information of the head mounted display device is transferred to the treatment guide device and used for generating information about a more accurate guide image.

In the present embodiment, the marker 150 includes four recognition balls 151 arranged apart from one another and recognized by the external detector, and a bracket 152 supporting the recognition balls 151 and coupled to the mount main body portion 111.

The nose rest N may be detachably coupled to the first connection arm 132. The nose rest N is manufactured in numerous types having various sizes so that a user may select and use an appropriate size according to the user body.

Furthermore, the head mounted display device according to the present embodiment includes a wire W supported on the head mount unit 110. The wire W may be connected to the display unit 120 to provide power thereto, and information may be transferred from the treatment guide device to the display unit 120 therethrough.

The operation of the head mounted display device according to the present embodiment is described below with reference to FIGS. 1 to 9 mainly for the position adjustment of the display unit 120.

First, in a case in which the position of the display unit 120 with respect to the eyes of a user is to be adjusted, when the display unit 120 needs to be away from the eyes of a user, a user holds and pushes the display unit 120 in a direction away from the eyes of a user. This operation causes the moving block 134 to move in a direction escaping from the first insertion hole 132a. In the movement process of the moving block 134, the locking protrusion 135 is inserted in a neighboring one in the preceding side of the locking recesses 134a so that the movement of the moving block 134 is made step by step.

In contrast, when the display unit 120 needs to be close to the eyes of a user, the user holds and pushes the display unit 120 in a direction close to the eyes of a user. This operation causes the moving block 134 to move in a direction to be inserted in the first insertion hole 132a.

Next, when the display unit 120 needs to be rotated with respect to the eyes of a user, the user hold and rotate the display unit 120. The display unit 120 is rotated around the hinge axis portion 137a by a rotation force applied by the user.

As such, as the head mounted display device according to the present embodiment includes the position adjustment unit 130 that moves the display unit 120 relative to the head mount unit 110 such that the position of the display unit 120 may vary with respect to the eyes of a user, the position of the display unit 120 with respect to the eyes of a user may be adjusted, and thus, the position and angle of the display unit 120 are adjusted corresponding to the different eye positions for different users, thereby increasing user's image recognition.

Although the present embodiment is described in detail with reference to the accompanying drawings, the scope of right of the present embodiment is not limited to the above drawings and descriptions.

While the present inventive concept has been described with respect to specific embodiments thereof, it will be apparent to those skilled in the art that various changes and modifications may be made without departing from the spirit and scope of the invention as defined in the following claims.

INDUSTRIAL APPLICABILITY

The present inventive concept may be used in the field of medical industry, particularly, dental medial industry.

The invention claimed is:

1. A head mounted display device comprising:
   a head mount unit wearable on a head of a user;
   a display unit supported on the head mount unit and sending an image to eyes of the user; and
   a position adjustment unit coupled to the head mount unit, connected to the display unit, and moving the display unit relative to the head mount unit such that a position of the display unit varies with respect to the eyes of the user,
   wherein the position adjustment unit comprises:
      a movement module moving the display unit in a direction approaching or receding from the head mount unit; and
      a rotation module connected to the movement module and rotating the display unit with respect to the head mount unit, and
   wherein the movement module comprises:
      a first connection arm connected to the head mount unit;
      a second connection arm connected to the display unit; and
      a moving block coupled to the second connection arm and coupled to the first connection arm to be movable relative thereto,
   wherein a first insertion hole, in which one end portion of the moving block is inserted, is formed in the first connection arm,
   wherein a second insertion hole, in which the other end portion of the moving block is inserted, is formed in the second connection arm, and
   wherein a plurality of locking recesses are formed in any one of one surface of the moving block and an inner wall surface of the first insertion hole, and a plurality of locking protrusions inserted in the locking recesses are formed on the other of the one surface of the moving block and the inner wall surface of the first insertion hole.

2. The head mounted display device of claim 1, wherein the locking recesses are formed in one surface of the moving block, and the locking protrusions are formed on the inner wall surface of the first insertion hole.

3. The head mounted display device of claim 1, wherein the rotation module is coupled to the second connection arm and includes a hinge axis portion to which the display unit is rotatably coupled.

4. The head mounted display device of claim 1, wherein the head mount unit comprises:
   a mount main body portion to which the position adjustment unit is connected, and which is formed in a ring shape so that the head of the user passes there through;
   a movable pad portion connected to the mount main body portion and moving in a direction approaching or receding from an inner wall surface of the mount main body portion; and
   a pad adjustment portion supported on the mount main body portion, connected to the movable pad portion, and moving the movable pad portion.

5. The head mounted display device of claim 1, wherein the display unit comprises:
   a display frame portion connected to the position adjustment unit;
   a source portion mounted on the display frame portion and outputting the image; and
   an optical portion supported on the display frame portion and transferring the image output from the source portion to the eyes of the user by reflecting the image.

6. The head mounted display device of claim 1, further comprising
   a face shield detachably attached to the display unit and shielding the face of the user.

7. The head mounted display device of claim 1, further comprising
   a marker coupled to the head mount unit and recognized by an external detector.

* * * * *